US012637417B2

(12) United States Patent
Tsuji et al.

(10) Patent No.: US 12,637,417 B2
(45) Date of Patent: May 26, 2026

(54) METHOD FOR PRODUCING 2-(HALOGENATED METHYL)NAPHTHALENE AND 2-NAPHTHYL ACETONITRILE

(71) Applicant: UBE Corporation, Ube-shi (JP)

(72) Inventors: Shunsuke Tsuji, Chiyoda-ku (JP); Masaki Nagahama, Chiyoda-ku (JP); Hirotsugu Taniike, Chiyoda-ku (JP)

(73) Assignee: UBE Corporation, Ube (JP)

( * ) Notice: Subject to any disclaimer, the term of this patent is extended or adjusted under 35 U.S.C. 154(b) by 233 days.

(21) Appl. No.: 18/007,370

(22) PCT Filed: Aug. 27, 2021

(86) PCT No.: PCT/JP2021/031570
§ 371 (c)(1),
(2) Date: Jan. 30, 2023

(87) PCT Pub. No.: WO2022/045304
PCT Pub. Date: Mar. 3, 2022

(65) Prior Publication Data

US 2024/0109840 A1 Apr. 4, 2024

(30) Foreign Application Priority Data

Aug. 31, 2020 (JP) ................................. 2020-146244

(51) Int. Cl.
*C07C 255/33* (2006.01)
*C07C 22/04* (2006.01)

(52) U.S. Cl.
CPC ............ *C07C 255/33* (2013.01); *C07C 22/04* (2013.01)

(58) Field of Classification Search
CPC .............................. C07C 255/33; C07C 22/04
See application file for complete search history.

(56) References Cited

U.S. PATENT DOCUMENTS

2008/0275253 A1 11/2008 Zhang et al.
2012/0157691 A1 6/2012 Zhang et al.
2014/0255662 A1 9/2014 Enomoto et al.
2021/0078940 A1* 3/2021 Nagahama .............. C07C 51/00

FOREIGN PATENT DOCUMENTS

JP 2001-39904 A 2/2001
JP 2009-511427 A 3/2009
WO WO 2013/047136 A1 4/2013
WO WO2019208807 A1 * 10/2018

OTHER PUBLICATIONS

Porta , Flow Chemistry: Recent Developments in the Synthesis of Pharmaceutical Products, 2016, Organic Process Research & Development, vol. 20, Issue 1, p. 2-25. (Year: 2016).*

Machine translation of JP2001039904A, retrieved on Jun. 9, 2025, pub. Feb. 13, 2001, p. 1-5. (Year: 2001).*

Japanese Notice of Reasons for Refusal issued Mar. 19, 2024 in Japanese Application No. 545740/2022, submitting English translation only, 8 pgs.

Indian Office Action issued Nov. 1, 2023 in Indian Application 202317005885, 7 pages.

International Search Report issued Oct. 5, 2021 in PCT/JP2021/031570, filed on Aug. 27, 2021, 3 pages.

Sasiambarrena et al., "Intramolecular sulfonylamidomethylation of 2-(2-naphthyl) and 2-(1-naphthyl)ethanesulfonamides: synthesis of new class of naphthosultams", Tetrahedron Letters, 2015, vol. 56, No. 16, pp. 2054-2058, Supplemental Information, pp. S1-S35.

Ni et al., "Carbocation Catalyzed Bromination of Alkyl Arenes, a Chemoselective $sp^3$ vs. $sp^2$ C—H functionalization", Advanced Synthesis & Catalysis, 2018, vol. 360, No. 21, pp. 4197-4204.

Amijs et al., "Carbon tetrachloride free benzylic brominations of methyl aryl halides", Green Chemistry, 2003, vol. 5, No. 4, pp. 470-474.

Cantillo et al., "A Scalable Procedure for Light-Induced Benzylic Brominations in Continuous Flow", The Journal. of Organic. Chemistry. 2014, vol. 79, pp. 223-229.

Extended European Search Report issued Aug. 9, 2024, in corresponding European Patent Application No. 21861725.6, 2 pages.

Yong Zhan: "Fluorescence response of anthracene modified D-[pi]-A heterocyclic chromophores containing nitrogen atom to mechanical force and acid vapor", Dyes and Pigments, 173, XP093187525, (2020) 108002, pp. 1-8.

Selective Benzylic Bromination of 2-Methylnaphthalene, Liladhar Waykolea et al., Synthetic Communication, vol. 27(12), 2159-2163 (1997).

Synthesis and application of new phenyl-functionalized zeolites as protection against radical bromination at the benzylic position, Akichika Itoh et al., Synlett, vol. 12, pp. 1450-1452, Dec. 31, 1997.

(Continued)

*Primary Examiner* — Adam C Milligan
*Assistant Examiner* — Karen Cheng
(74) *Attorney, Agent, or Firm* — Oblon, McClelland, Maier & Neustadt, L.L.P.

(57) ABSTRACT

A method for producing a 2-(halogenated methyl)naphthalene represented by general formula (1):

(1)

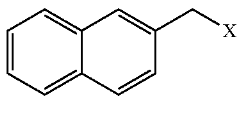

where X is a halogen atom. The method includes a halogenation process of reacting 2-methylnaphthalene with a halogenating agent under light irradiation, in an organic solvent selected from a halogenated hydrocarbon, an aliphatic ester and an aliphatic hydrocarbon.

4 Claims, 1 Drawing Sheet

(56) References Cited

OTHER PUBLICATIONS

Office Action issued on Feb. 15, 2026, in the corresponding Chinese application No. 202180059790.9 (with English translation), citing document 1 and 2 therein.

* cited by examiner

METHOD FOR PRODUCING 2-(HALOGENATED METHYL)NAPHTHALENE AND 2-NAPHTHYL ACETONITRILE

CROSS REFERENCE TO RELATED APPLICATIONS

This application is a National Stage entry under 35 U.S.C. § 371 of PCT/JP2021/031570, filed on Aug. 27, 2021, and claims priority to Japanese Patent Application No. 2020-146244, filed on Aug. 31, 2020. The entire contents of both are incorporated herein by reference.

TECHNICAL FIELD

The present invention relates to methods for producing 2-(halogenated methyl) naphthalenes and 2-naphthylacetonitrile useful as synthetic intermediates for pharmaceuticals and the like.

BACKGROUND ART 2-(Halogenated methyl)naphthalenes are useful as synthetic raw materials or synthetic intermediates for various pharmaceuticals, agrochemicals, chemical products and the like. Naphthalene compounds having chemical structures similar to 2-(halogenated methyl)naphthalenes are also expected to be used as synthetic raw materials or synthetic intermediates for various pharmaceuticals, agrochemicals and chemical products. For example, 2-(halogenated methyl)naphthalenes, and 2-naphthylacetonitrile having a chemical structure similar thereto are useful as synthetic raw materials or synthetic intermediates for therapeutic drugs for attention deficit hyperactivity disorder (ADHD). Specifically, for example, 2-(halogenated methyl)naphthalenes and 2-naphthylacetonitrile can be preferably used as synthetic raw materials or synthetic intermediates for (1R,5S)-1-(naphthalen-2-yl)-3-azabicycio[3.1.0]hexane (common name: Centanafadine).

Batch reaction methods are known as conventional production methods for producing 2-(halogenated methyl)naphthalenes. For example, a method for producing 2-(bromomethyl)naphthalene by placing 2-methylnaphthalene, N-bromosuccinimide, dichloromethane, benzene and trityl fluoroborate in a batch reactor, and then subjecting the mixture to a photoreaction under light irradiation at room temperature is known (Non-Patent Document 1). Photoreaction refers to all chemical reactions in which molecules are excited to a higher energy level state by absorbing energy through light irradiation, and the excited molecules cause a reaction, and it is also called photochemical reaction.

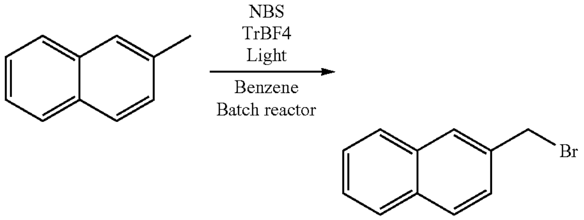

However, the method described in Non-Patent Document 1 is a reaction using benzene solvent, and the industrial use of benzene solvent is extremely difficult for safety reasons, and the yield of the obtained 2-(bromomethyl)naphthalene is also not industrially satisfactory. Therefore, a safer, more productive and industrial production method is desired.

In recent years, continuous halogenation reaction methods for increasing productivity are known. For example, a method for continuously producing 4-tert-butylbenzyl bromide by subjecting a solution prepared by mixing 4-tert-butyltoluene and N-bromosuccinimide in an acetonitrile solvent, to photoirradiation in a flow photochemical reactor is known (Non-Patent Document 2).

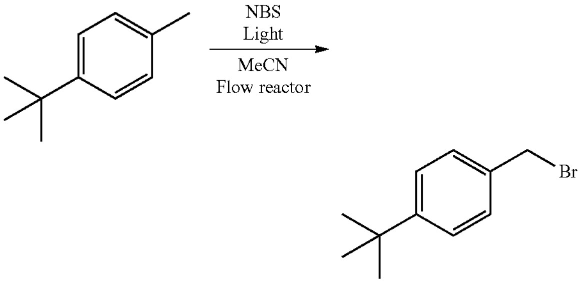

However, as is clear from Comparative Example 1 below, it was found that the replacement of 4-tert-butyltoluene, the substrate described in Non-Patent Document 2, with 2-methylnaphthalene did not yield the target compound 2-(bromomethyl)naphthalene with high selectivity, but instead undesirable 1-bromo-2-methylnaphthalene as the major product.

Therefore, for production of 2-(halogenated methyl)naphthalenes in high yield, a production method that enables highly selective halogenation of the methyl at the 2-position of 2-methylnaphthalene is desired.

Non-Patent Document 3 describes the production of 2-naphthylacetonitrile by subjecting 2-(halogenated methyl) naphthalenes to cyanation.

CITATION LIST

Non-Patent Document

[Non-Patent Document 1] Adv. Synth. Catal. (2018) 4197-4204

[Non-Patent Document 2] JOC. (2014) 223-229

[Non-Patent Document 3] Tetrahedron Letters 56 (2015) 2054-2058

SUMMARY OF INVENTION

Problems to be Solved by the Invention

The present invention aims to provide a method for producing 2-(halogenated methyl)naphthalenes, and a method for producing 2-naphthylacetonitrile therefrom, both safely and inexpensively with high selectivity in good yield.

Means of Solving the Problems

The present inventors have conducted intensive studies and found that the reaction of 2-methylnaphthalene with a halogenating agent in a specific organic solvent under light irradiation yields 2-(halogenated methyl)naphthalenes and then 2-naphthylacetonitrile therefrom, both safely and inexpensively with high selectivity in good yield, which resulted in the completion of the present invention. Accordingly, the present invention is characterized by the following

[1] A method for producing a 2-(halogenated methyl) naphthalene represented by general formula (1):

(1)

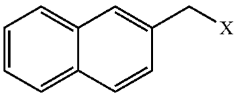

wherein X is a halogen atom, which comprises a halogenation process of reacting 2-methylnaphthalene with a halogenating agent under light irradiation, in an organic solvent selected from a halogenated hydrocarbon, an aliphatic ester and an aliphatic hydrocarbon.

[2] The method according to the above [1], wherein the halogenating agent is a brominating agent.

[3] The method according to [1] or [2], wherein the light irradiation is performed using light with a wavelength of 280 nm to 700 nm.

[4] The method according to any one of [1] to [3], wherein the reaction is carried out within the range of −20° C. to 100° C.

[5] The method according to any one of [1] to [4], wherein the reaction is carried out in the absence of an additive.

[6] The method according to any one of [1] to [5], wherein the reaction is carried out by flow synthesis reaction.

[7] A method for producing 2-naphthylacetonitrile, which comprises a halogenation process of reacting 2-methylnaphthalene with a halogenating agent under light irradiation, in an organic solvent selected from a halogenated hydrocarbon, an aliphatic ester and an aliphatic hydrocarbon; and a cyanation process of reacting the 2-(halogenated methyl)naphthalene obtained in the halogenation process and represented by general formula (1):

(1)

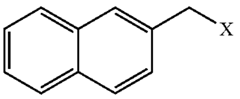

wherein X is a halogen atom, with a cyanating agent, in a solvent.

Effect of the Invention

According to the method for producing 2-(halogenated methyl)naphthalenes of the present invention, 2-(halogenated methyl)naphthalenes can be produced safely and inexpensively with high selectivity in good yield. Moreover, according to the method for producing 2-naphthylacetonitrile of the present invention, 2-naphthylacetonitrile can be produced safely and inexpensively with high selectivity in good yield.

DESCRIPTION OF EMBODIMENTS

The present invention will be explained in detail below.

[Method for Producing 2-(Halogenated Methyl) Naphthalenes]

The method for producing 2-(halogenated methyl)naphthalenes of the present invention is a method for producing a 2-(halogenated methyl)naphthalene represented by general formula (1):

(1)

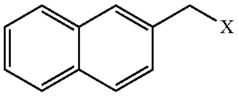

wherein X is a halogen atom, (hereinafter, this compound may be referred to as a halogenated naphthalene) by selective halogenation of the methyl at the 2-position of 2-methylnaphthalene employing a reaction with a halogenating agent under light irradiation, in an organic solvent selected from a halogenated hydrocarbon, an aliphatic ester and an aliphatic hydrocarbon (hereinafter, this process may be referred to as "the halogenation process of the present invention").

"Halogen atom" used herein means a fluorine atom, a chlorine atom, a bromine atom or an iodine atom. The "halogen atom" is preferably a chlorine atom, a bromine atom or an iodine atom, particularly preferably a bromine atom in terms of reactivity.

<<Halogenation Process>>

Figure 1:
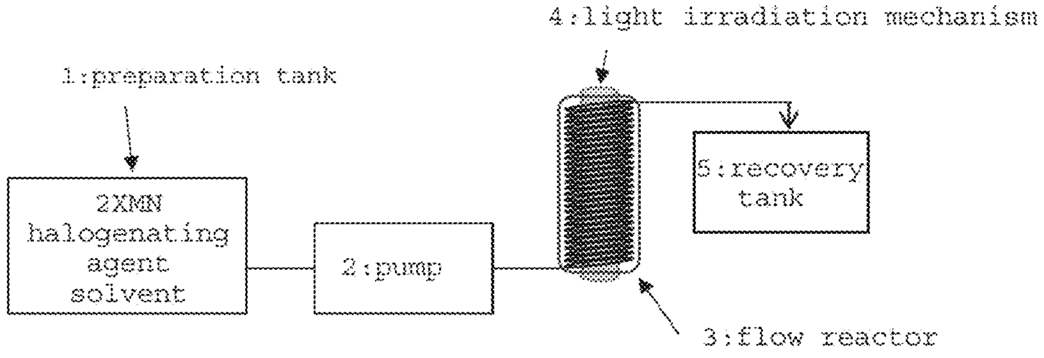
FIG. 1 is a system diagram of a flow synthesis reactor showing one example of embodiments of the method for producing 2-(halogenated methyl)naphthalenes of the present invention.

Examples of the method for carrying out the halogenation process of the present invention include a method of mixing 2-methylnaphthalene, a halogenating agent and an organic solvent in a batch reactor, and then reacting the mixture by light irradiation under the reaction condition. Moreover, a method as shown in FIG. 1 is also included; a method using a flow synthesis reactor in which a mixed solution of 2-methylnaphthalene (2MN), an organic solvent and a halogenating agent, which is prepared in preparation tank 1, is continuously supplied by pump 2 while light-irradiating to permeable flow reactor 3 equipped with light irradiation mechanism 4, and the 2-methylnaphthalene is continuously subjected to halogenation in flow reactor 3, and the reaction solution containing a 2-(halogenated methyl)naphthalene flowing out of flow reactor 3 is recovered in recovery tank 5.

The halogenation process of the present invention is preferably carried out by flow synthesis reaction using a flow synthesis reactor in terms of reactivity and selectivity. This flow synthesis reactor will be explained later.

<2-Methylnaphthalene>

2-Methylnaphthalene, which is a raw material for producing 2-(halogenated methyl)naphthalenes, may be commercially available, or obtained by a known method or a method analogous thereto.

<Organic Solvent>

The organic solvent used in the present invention is selected from a halogenated hydrocarbon, an aliphatic ester and an aliphatic hydrocarbon, which may be used alone or in combination of two or more in any ratio. The use of a halogenated hydrocarbon or an aliphatic ester alone is preferred in terms of reactivity.

Halogenated hydrocarbons are aliphatic hydrocarbons substituted with one or more halogen atoms, and include halogenated aliphatic hydrocarbons having generally 1 to 10 carbon atoms, preferably 1 to 8 carbon atoms, particularly preferably 1 to 6 carbon atoms.

Examples of the halogenated hydrocarbon include dichloromethane, chloroform, carbon tetrachloride, trichloroethylene, tetrachloroethylene, dichloroethane and 1,1,2,2-tetrachloroethane. Dichloromethane and dichloroethane are preferred, and dichloromethane is particularly preferred, in terms of reactivity, selectivity, safety and availability.

Aliphatic esters are aliphatic hydrocarbons having one or more ester bonds, and include aliphatic esters having generally 1 to 10 carbon atoms, preferably 1 to 8 carbon atoms, particularly preferably 1 to 6 carbon atoms.

Examples of the aliphatic ester include acetates such as methyl acetate, ethyl acetate and propyl acetate. Methyl acetate and ethyl acetate are preferred in terms of reactivity, selectivity and availability, and methyl acetate is particularly preferred in terms of safety.

Aliphatic hydrocarbons are cyclic or chain aliphatic hydrocarbons, and include aliphatic hydrocarbons having generally 5 to 12 carbon atoms, preferably 5 to 10 carbon atoms, particularly preferably 5 to 8 carbon atoms.

Examples of the cyclic aliphatic hydrocarbon include cyclopentane, cyclohexane, cycloheptane, cyclooctane, methylcyclopentane, ethylcyclopentane, methylcyclohexane, ethylcyclohexane, 1,2-dimethylcyclohexane, 1,3-dimethylcyclohexane, 1,4-dimethylcyclohexane, isopropylcyclohexane, n-propylcyclohexane, t-butylcyclohexane, n-butylcyclohexane and isobutylcyclohexane. Cyclopentane, cyclohexane, cycloheptane and cyclooctane are preferred, and cyclopentane, cyclohexane and cycloheptane are particularly preferred, in terms of reactivity.

Examples of the chain aliphatic hydrocarbon include n-pentane, n-hexane, n-heptane, n-octane and the like, and n-hexane and n-heptane are preferred in terms of reactivity.

The amount of the organic solvent to be used is generally 1 times by weight to 200 times by weight, preferably 2 times by weight to 150 times by weight, particularly preferably 3 times by weight to 100 times by weight, relative to 2-methylnaphthalene, in terms of productivity and reactivity.

In the present invention, it is usually preferable to dissolve 2-methylnaphthalene and a halogenating agent as raw materials in an organic solvent, and then proceed the reaction in a homogeneous solution form. In some cases, the raw materials may be in a slurry form without being completely dissolved.

<Halogenating Agent>

The halogenating agent is not particularly limited as long as it can halogenate 2-methylnaphthalene. Examples of the halogenating agent include brominating agents, iodinating agents and chlorinating agents. The use of brominating agents is preferred in terms of reactivity. The halogenating agent may be used in combination of two or more in any ratio, preferably used alone in terms of cost and reactivity.

Examples of the brominating agent include N-bromosuccinimide, 1,3-dibromo-5,5-dimethylhydantoin, N,N,N',N'-tetrabromobenzene-1,3-disulfonamide and molecular bromine. N-Bromosuccinimide and 1,3-dibromo-5,5-dimethylhydantoin are preferred, and N-bromosuccinimide is particularly preferred, in terms of reactivity, Examples of the chlorinating agent include N-chlorosuccinimide, 1,3-dichloro-5,5-dimethylhydantoin and molecular chlorine. N-Chlorosuccinimide is preferred in terms of reactivity.

Examples of the iodinating agent include N-iodosuccinimide, 1,3-diiodo-5,5-dimethylhydantoin and molecular iodine. N-Iodosuccinimide is preferred in terms of reactivity.

The amount of the halogenating agent to be used varies depending on the kind of the halogenating agent to be used, and it is not limited as long as it is sufficient to halogenate 2-methylnaphthalene. The lower limit of the halogen atom content in the halogenating agent is generally 1 mol or more, and the upper limit is generally 10 mol or less, preferably 5 mol or less, particularly preferably 2 mol or less, per 1 mol of 2-methylnaphthalene.

<Other Additives>

In the present invention, additives such as catalysts and photosensitizers may be used as necessary. However, in the present invention, the reaction can be carried out well without using any additive, so it is generally preferable to carry out the reaction in the absence of any additive.

If a photosensitizer is used as an additive, known photosensitizers such as benzophenone, 4,4-bis(dimethoxy)thiobenzophenone, 4,4-bis(dimethylamino)benzophenone, 4,4-bis(dimethylamino)thiobenzophenone and 4,4-bis(dimethoxy)benzophenone can be used alone or in combination of two or more in any ratio.

The amount of the photosensitizer to be used is generally 0.01 mol % to 10 mol %, per 1 mol of 2-methylnaphthalene, in terms of reactivity.

<Reaction Condition>

(Reaction Temperature)

As for the reaction temperature in the halogenation process of the present invention, the lower limit is generally −20° C. or higher, preferably −10° C. or higher, particularly preferably 0° C. or higher, and the upper limit is generally 100° C. or lower, preferably 90° C. or lower, particularly preferably 80° C. or lower, in terms of reactivity, productivity and the like. If the reaction temperature is too low, reactivity may decrease. On the other hand, if the temperature is too high, side reactions may occur, and yield and selectivity may decrease.

(Reaction Pressure)

The halogenation process of the present invention can be carried out under normal or increased pressure, and for example, the lower limit is generally 0.1 MPa or higher, and the upper limit is generally 1 MPa or lower, preferably 0.8 MPa or lower, particularly preferably 0.6 MPa or lower. In the present invention, the reaction can be efficiently carried out by adjusting the pressure by applying back pressure to the flow path of the reactor to be used with a back pressure valve or the like.

(Reaction Time)

The reaction time of the halogenation process of the present invention means the time (residence time) during which the raw material mixture (a mixed solution of 2-methylnaphthalene, a halogenating agent and an organic solvent) remains in the photochemical reactor used in the present invention. The reaction time varies depending on the reaction temperature and reaction pressure, and it is generally 0.1 min to 240 min, preferably 1 min to 120 min. In the case of a continuous reaction using a flow synthesis reactor or the like as a photochemical reactor, the reaction time means the residence time of the raw material mixture under light irradiation.

(Reaction Atmosphere)

The halogenation process of the present invention can be carried out in a nitrogen atmosphere or in an oxygen-containing atmosphere such as an air atmosphere. The halogenation process is preferably carried out in an oxygen-containing atmosphere in terms of reactivity.

(Wavelength of Light)

The wavelength of light to be irradiated can be appropriately selected depending on the organic solvent used. It preferably contains light with a wavelength of generally 270 nm to 800 nm, preferably 280 nm to 700 nm, further more preferably 290 nm to 600 nm, particularly preferably 300 nm to 550 nm, in terms of reactivity and selectivity. In the present invention, the wavelength of light means the emission wavelength of a light source.

(Radiant Flux of Light)

The radiant flux of light of the present invention is generally 1 J/sec to 4000 J/sec, preferably 2 J/sec to 3000 J/sec, particularly preferably 3 J/sec to 2000 J/sec, in terms of reactivity.

(Reaction Mode)

In the present invention, 2-methylnaphthalene is reacted with a halogenating agent under light irradiation in the specific organic solvent described above, and the reaction mode is not particularly limited. In terms of reactivity, the reaction is industrially preferably carried out using a flow synthesis reactor (flow reactor) equipped with a light irradiation mechanism. For example, as shown in FIG. 1, a mixed solution of 2-methylnaphthalene (2MN), a halogenating agent and an organic solvent is prepared in preparation tank 1, supplied by pump 2 to flow synthesis reactor (flow reactor) 3, and subjected to a halogenation reaction in flow synthesis reactor 3 under desired light irradiation by light irradiation mechanism 4, and the reaction solution is recovered in recovery tank 5.

(Photochemical Reactor)

The material of the photochemical reactor used in the present invention is not particularly limited as long as it has excellent chemical resistance and transmits a light from a light source. Examples thereof include glass, transparent synthetic resins having chemical resistance, and the like. Also, the size of the photochemical reactor can be appropriately selected depending on the scale of production.

The type of photochemical reactor is not particularly limited, but a batch reactor or a flow synthesis reactor can be used.

(Batch Reactor)

A batch reactor equipped with a flow path for introducing and discharging a substrate and the like, a temperature-controllable jacket, a stirrer, and the like can be used.

(Flow Synthesis Reactor)

A flow synthesis reactor is usually tubular. The size of the tube can be appropriately selected depending on the scale of production, and for example, the inner diameter is generally 1 mm to 20 mm. The length of the tube can be appropriately selected depending on the desired residence time. The shape of the tube is usually straight, curved or helical, and the particularly preferred is helical in terms of reactivity.

The flow synthesis reactor may also be equipped with a temperature control mechanism.

A substrate and the like can be quantitatively introduced into and discharged from the flow synthesis reactor by supply using a syringe pump, diaphragm pump, mass controller, or the like. The flow path on the outflow side of the reaction solution from the flow synthesis reactor may be equipped with a back pressure valve or an in-line analyzer.

(Light Irradiation Mechanism)

In the present invention, the photochemical reactor is preferably equipped with a light irradiation mechanism for light irradiation.

For example, when the photochemical reactor is a flow synthesis reactor, it preferably has a structure that enables the predetermined light irradiation to the tube where the reaction takes place. For example, as shown in FIG. 1, the preferred is a helical tube reactor equipped inside with a light irradiation mechanism with a light source.

<Work-Up>

The target product 2-(halogenated methyl)naphthalene is isolated by a conventional method from the reaction solution obtained in the halogenation process of the present invention. The isolation can be performed, for example, by mixing the obtained reaction solution with water or an alkali aqueous solution for neutralization, concentrating the organic layer obtained by separating the mixture, precipitating the target product, and subjecting to solid-liquid separation. If necessary, known purification means such as recrystallization and column chromatography may be performed.

<Use of 2-(Halogenated Methyl)Naphthalenes>

2-(Halogenated methyl)naphthalenes obtained in the present invention can be used as raw materials for various medicaments or intermediates thereof. For example, 2-naphthylacetonitrile, which is useful as a synthetic raw material or synthetic intermediate of centanaphadin, a therapeutic drug for attention deficit hyperactivity disorder (ADHD), can be produced in high yield, for example by subjecting a 2-(halogenated methyl)naphthalene obtained in the present invention to cyanation.

[Method for Producing 2-Naphthylacetonitrile]

2-Naphthylacetonitrile can be produced by reacting a 2-(halogenated methyl)naphthalene obtained by the above method with a cyanating agent in a solvent (hereinafter, this process may be referred to as "the cyanation process of the present invention").

<<Cyanation Process>>

Figure 2:
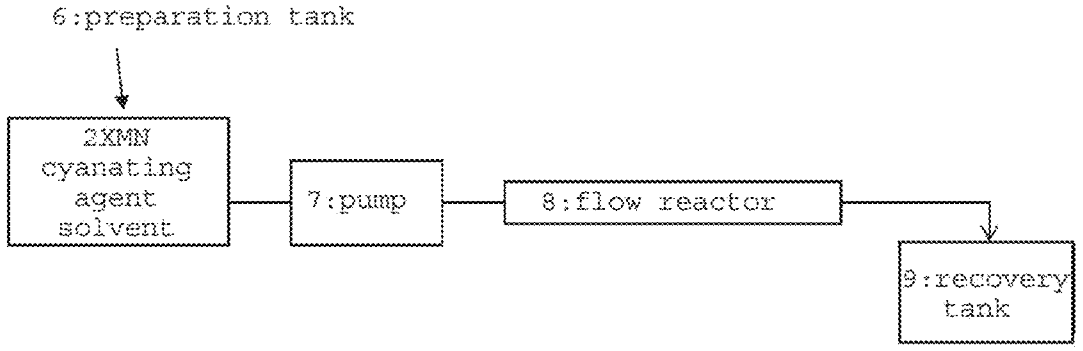
FIG. 2 is a system diagram of a flow synthesis reactor showing one example (cyanation process) of embodiments of the method for producing 2-naphthylacetonitrile of the present invention.

Examples of the method for carrying out the cyanation process of the present invention include a method of mixing a 2-(halogenated methyl)naphthalene, a cyanating agent and a solvent in a batch reactor, and then reacting the mixture under the reaction condition. Moreover, a method as shown in FIG. 2 is also included; a method in which a mixed solution of a 2-(halogenated methyl)naphthalene, a solvent and a cyanating agent, which is prepared in preparation tank 6, is continuously supplied by pump 7 to flow reactor 8, and the 2-(halogenated methyl)naphthalene is continuously subjected to a cyanation reaction in flow reactor 8, and the reaction solution containing 2-naphthylacetonitrile flowing out of flow reactor 8 is recovered in recovery tank 9.

The cyanation process may also be carried out according to known methods such as the method described in Non-Patent Document 3.

<Solvent>

As solvents, aqueous solvents such as water and organic solvents such as alcohols and nitriles can be used alone or in combination of two or more in any ratio. A mixed solvent of water and a nitrile is preferred in terms of cost and reactivity.

Aqueous solvents include water such as pure water, ion-exchanged water and industrial water, and a mixture of water and appropriate hydrophilic organic solvents such as ketones, alcohols and glycol ethers. Water is preferred in terms of cost and reactivity.

Alcohols include aliphatic alcohols having 1 to 10 carbon atoms, preferably 1 to 8, particularly preferably 1 to 6 carbon atoms. Examples of the alcohol include methanol, ethanol, propanol, butanol, pentanol and hexanol. Methanol and ethanol are preferred in terms of cost and reactivity.

Nitriles mean organic compounds having a structure represented by R–C≡N wherein R is an aliphatic hydrocarbon group having 1 to 10 carbon atoms, preferably 1 to 8 carbon atoms, particularly preferably 1 to 6 carbon atoms. Examples thereof include acetonitrile and propionitrile. Acetonitrile is preferred in terms of reactivity.

The organic solvent is preferably a nitrile, particularly preferably acetonitrile, in terms of cost and reactivity.

The amount of the solvent to be used is generally 1 times by weight to 200 times by weight, preferably 2 times by weight to 150 times by weight, particularly preferably 3 times by weight to 100 times by weight, relative to the 2-(halogenated methylnaphthalene, in terms of productivity and reactivity.

<Cyanating Agent>

Examples of the cyanating agent include inorganic cyanating agents such as sodium cyanide, potassium cyanide and lithium cyanide, and organic cyanating agents such as tetrabutylammonium cyanide. Inorganic cyanating agents are preferred in terms of reactivity. The inorganic cyanating agent is preferably sodium cyanide or potassium cyanide, particularly preferably sodium cyanide in terms of reactivity.

The amount of the cyanating agent to be used is generally 1 mol to 10 mol, preferably 1 mol to 5 mol, particularly preferably 1 mol to 2 mol, per 1 mol of the 2-(halogenated methyl)naphthalene, in terms of reactivity.

<Reaction Condition>

(Reaction Temperature)

As for the reaction temperature in the cyanation process of the present invention, the lower limit is generally 0° C. or higher, preferably 20° C. or higher, particularly preferably 40° C. or higher, and the upper limit is generally 100° C. or lower, preferably 90° C. or lower, particularly preferably 80° C. or lower, in terms of reactivity, productivity and the like, (Reaction Time)

The reaction time of the cyanation process of the present invention is generally 0.1 hr to 24 hr, preferably 1 hr to 12 hr.

(Reaction Pressure)

As for the reaction pressure in the cyanation process of the present invention, the lower limit is generally 0.1 MPa or higher, and the upper limit is generally 1 MPa or lower.

(Supply Method)

The supply order of a 2-(halogenated methyl)naphthalene, a cyanating agent and a solvent can be appropriately selected. When a batch reactor is used, for example, the reaction can be carried out under the reaction condition by supplying a mixed solution of a cyanating agent and a solvent to a mixed solution of a 2-(halogenated methyl) naphthalene and a solvent as a bed liquid.

When a flow synthesis reactor is used, each raw material may be supplied in one batch or several batches. For example, the reaction can be carried out under the reaction condition by supplying a mixed solution of a 2-(halogenated methyl)naphthalene, a cyanating agent and a solvent to a flow synthesis reactor. The reaction can also be carried out by supplying a mixed solution of a cyanating agent and a solvent to a flow synthesis reactor, while circulating a mixed solution of a 2-(halogenated methyl)naphthalene and a solvent through the flow synthesis reactor.

<Reaction Mode>

The reaction can be carried out employing the batch reaction or flow reaction described above.

<Reactor>

The reaction can be carried out using the flow synthesis reactor or batch reactor described above.

<Work-Up>

The target product 2-naphthylacetonitrile is isolated by a conventional method from the reaction solution obtained in the cyanation process of the present invention. The isolation may be performed, for example, by treatments such as neutralization, solid-liquid separation, concentration and filtration of the obtained reaction solution, or by known purification means crystallization and column chromatography.

EXAMPLES

Next, the present invention will be explained in more detail with reference to the following Examples, but the present invention is not limited to these examples as long as it does not deviate from the gist thereof. In the following Examples and Comparative Examples, unless otherwise noted, the reaction time is light irradiation time. The conversion and selectivity were calculated according to the following formulas. A(C) in the formulas means the area ratio (%) of Compound C in the analysis result under Analysis Condition 1. For example, A(2MN) means the area ratio (%) of the area value of 2MN to the total area value in the analysis result under Analysis Condition 1.

[Formula for conversion]

$$\text{conversion [\%]} = \left(1 - \frac{A(2MN)}{A(2MN) + A(2BMN) + A(2DBMN) + A(1BMN) + A(1B2BMN) + A(\text{others})}\right) \times 100$$

[Formula for selectivity]

$$\text{selectivity [\%]} = \frac{A(2BMN)}{A(2BMN) + A(2DBMN) + A(1BMN) + A(1B2BMN)} \times 100$$

Abbreviation

In the present specification, each abbreviation means the following compounds.

2MN: 2-methylnaphthalene
2XMN: 2-(halogenated methyl)naphthalene
2BMN: 2-(bromomethyl)naphthalene
2DBMN: 2-(dibromomethyl)naphthalene
1BMN: 1-bromo-2-methylnaphthalene
1B2BMN: 2-(bromomethyl)-1-bromonaphthalene
NpAN 2-naphthylacetonitrile
DCM: dichloromethane
DCE: dichloroethane
MeCN: acetonitrile
c-Hex: cyclohexane
AT: acetone
AcOMe: methyl acetate
IPA: isopropanol
NBS: N-bromosuccinimide
DMDBH: 1,3-dibromo-5,5-dimethylhydantoin

[Flow Synthesis Reactor]

In Examples and Comparative Examples, a commercially available flow synthesis reactor ("Photo Flow System T-1" manufactured by Asahi Lab Commerce, Inc., volume 6 mL) shown in FIG. 1 was used.

[Light Source]

In Examples and Comparative Examples, light sources used for light irradiation are as shown in Table 1. Note that the range of emission wavelength includes a measurement error of about ±10 nm.

TABLE 1

| light source | manufacturer | product number | emission wavelength [nm] | radiant flux [J/min] |
|---|---|---|---|---|
| Light Source 1 | Sankyo Denki Co., Ltd. | FL4BLB | 300-400 | 4 |
| Light Source 2 | Sankyo Denki Co., Ltd. | TL4W/865 | 380-800 | 4 |
| Light Source 3 | Panasonic Corporation | FL4WF | 380-750 | 4 |

[Analysis Method]

In the following Examples and Comparative Examples, apparatuses and conditions used for analysis of reaction solution are as shown in Tables 2 and 3.

[Analysis Method 1 (HPLC)]

TABLE 2

| | | |
|---|---|---|
| apparatus | Agilent 1100 manufactured by Agilent Technologies Japan, Ltd. | |
| detector | ultraviolet absorptiometry (measurement wavelength: 215 nm) | |
| column | Cadenza CD-C18, 3 μm, 150 mm × 4.6 mm | |
| column temperature | constant temperature around 40° C. | |
| mobile phase | A | 0.1 vol % aqueous trifluoroacetic acid solution |
| | B | acetonitrile |
| gradient | 0 min (B: 15%) - 15 min (B: 90%) - 20 min (B: 90%) | |
| diluent | acetonitrile | |
| flow rate | 1.0 mL/min | |
| injection | 5 μL | |
| retention time | 2BMN: 14.9 min<br>2MN: 15.4 min<br>2DBMN: 15.9 min<br>1B2BMN: 16.6 min<br>1BMN: 17.5 min | |

[Analysis Method 2 (HPLC)]

TABLE 3

| | | |
|---|---|---|
| apparatus | Agilent 1100 manufactured by Agilent Technologies Japan, Ltd. | |
| detector | ultraviolet absorptiometry (measurement wavelength: 280 nm) | |
| column | Cadenza CD-C18, 3 μm, 150 mm × 4.6 mm | |
| column temperature | constant temperature around 40° C. | |
| mobile phase | A | 0.1 vol % aqueous trifluoroacetic acid solution |
| | B | acetonitrile |
| gradient | 0 min (B: 15%) - 15 min (B: 90%) - 20 min (B: 90%) | |
| diluent | acetonitrile | |
| flow rate | 1.0 mL/min | |
| injection | 5 μL | |
| retention time | 2NPAN: 11.8 min<br>2BMN: 14.9 min | |

Example 1

The reaction was carried out by flowing a mixed solution (2MN: 0.1 mol/L, NBS: 0.105 mol/L), which was prepared by dissolving 2MN and NBS as a halogenating agent in DCM, by its supply, through a flow synthesis reactor maintained at a jacket temperature of 20° C. so that the reaction time was 25 minutes, in an air atmosphere and under light irradiation from Light Source 1. At that time, the supply rate of the mixed solution was kept at 240 μL/min using a diaphragm pump.

The obtained reaction solution was analyzed by Analysis Method 1. The results are shown in Table 4. The obtained reaction solution contained 2BMN (chemical purity 94.2%, selectivity 100.0%).

2BMN:

$^1$H-NMR (400 MHz, $CDCL_3$): δ 7.84-7.80 (m, 4H), 7.52-7.48 (m, 3H), 4.67 (s, 2H)

Examples 2 to 4

The reaction was carried out in the same manner as in Example 1, except that the kind of organic solvent, the concentration of 2MN, and the amount of halogenating agent used were changed as shown in Table 4. The obtained reaction solution was analyzed in the same manner as in Example 1. The results are shown in Table 4.

Comparative Examples 1 to 3

The reaction was carried out in the same manner as in Example 1, except that the kind of organic solvent, the concentration of 2MN, and the amount of halogenating agent used were changed as shown in Table 4. The obtained reaction solution was analyzed in the same manner as in Example 1. The results are shown in Table 4.

TABLE 4

| | organic solvent | 2MN concentration [mol/L] | halogenating agent [mol eq.] | HPLC analysis results of reaction solution [Area %] 2MN | 2BMN | 2DBMN | 1BMN | 1B2BMN | Others | conversion [%] | selectivity [%] |
|---|---|---|---|---|---|---|---|---|---|---|---|
| Ex. 1 | DCM | 0.1 | 1.05 | 5.8 | 94.2 | 0.0 | 0.0 | 0.0 | 0.0 | 94.2 | 100.0 |
| Ex. 2 | c-Hex | 0.1 | 1.05 | 72.9 | 24.2 | 0.0 | 0.0 | 0.0 | 2.9 | 27.1 | 100.0 |
| Ex. 3 | c-Hex | 0.5 | 1.50 | 10.4 | 86.5 | 0.1 | 0.0 | 0.0 | 3.0 | 89.6 | 99.9 |
| Ex. 4 | DCE | 0.1 | 1.05 | 10.8 | 83.9 | 3.9 | 0.2 | 0.4 | 0.9 | 89.2 | 94.9 |
| Com. Ex. 1 | MeCN | 0.5 | 1.05 | 20.8 | 0.0 | 0.0 | 79.2 | 0.0 | 0.0 | 79.2 | 0.0 |
| Com. Ex. 2 | AT | 0.5 | 1.05 | 52.5 | 34.5 | 0.0 | 13.0 | 0.0 | 0.0 | 47.5 | 72.7 |
| Com. Ex. 3 | IPA | 0.1 | 1.05 | 100.0 | 0.0 | 0.0 | 0.0 | 0.0 | 0.0 | 0.0 | — |

As is clear from the results of Examples 1 to 4 and Comparative Examples 1 to 3 shown in Table 4, 2BMN can be efficiently obtained with high conversion and selectivity by using a halogenated hydrocarbon or an aliphatic hydrocarbon as an organic solvent.

When MeCN, which was used to obtain 2BMN in Non-Patent Document 2, was used as an organic solvent, surprisingly, the target product 2BMN was not obtained (Comparative Example 1). When AT was used as an organic solvent, it is clear that the selectivity is not good because a large amount of 1BMN in which the naphthalene ring is brominated, was produced (Comparative Example 2). When IPA was used as an organic solvent, the reaction did not proceed (Comparative Example 3).

Examples 5 and 6

The reaction was carried out in the same manner as in Example 1, except that the kind and the amount of halogenating agent used were changed as shown in Table 5. The obtained reaction solution was analyzed in the same manner as in Example 1. The results are shown in Table 5.

TABLE 5

| Ex. | halogenating agent | halogenating agent [mol eq.] | HPLC analysis results of reaction solution [Area %] 2MN | 2BMN | 2DBMN | 1BMN | 1B2BMN | Others | conversion [%] | selectivity [%] |
|---|---|---|---|---|---|---|---|---|---|---|
| Ex. 5 | DMDBH | 0.50 | 14.9 | 85.1 | 0.0 | 0.0 | 0.0 | 0.0 | 85.1 | 100.0 |
| Ex. 6 | DMDBH | 0.60 | 0.0 | 95.9 | 4.1 | 0.0 | 0.0 | 0.0 | 100.0 | 95.9 |

As is clear from the results of Examples 5 and 6 shown in Table 5, 2BMN can be efficiently obtained with high conversion and selectivity, even when a brominating agent other than NBS is used.

Examples 7 and 8

The reaction was carried out in the same manner as in Example 1, except that the light source was changed as shown in Table 6. The obtained reaction solution was analyzed in the same manner as in Example 1. The results are shown in Table 6.

TABLE 6

| Ex. | light source | emission wavelength [nm] | HPLC analysis results of reaction solution [Area %] 2MN | 2BMN | 2DBMN | 1BMN | 1B2BMN | Others | conversion [%] | selectivity [%] |
|---|---|---|---|---|---|---|---|---|---|---|
| Ex. 7 | Light Source 2 | 380-800 | 4.6 | 95.4 | 0.1 | 0.0 | 0.0 | 0.0 | 95.4 | 99.9 |
| Ex. 8 | Light Source 3 | 380-750 | 7.2 | 92.7 | 0.0 | 0.0 | 0.0 | 0.0 | 92.8 | 100.0 |

As is clear from the results of Examples 7 and 8 shown in Table 6, 2BMN can be efficiently obtained with high conversion and selectivity, even when the light source is changed.

Examples 9 and 10

The reaction was carried out in the same manner as in Example 1, except that the reaction temperature and the residence time were changed as shown in Table 7. The obtained reaction solution was analyzed in the same manner as in Example 1. The results are shown in Table 7.

TABLE 7

| Ex. | reaction temperature [° C.] | reaction time [min] | HPLC analysis results of reaction solution [Area %] 2MN | 2BMN | 2DBMN | 1BMN | 1B2BMN | Others | conversion [%] | selectivity [%] |
|---|---|---|---|---|---|---|---|---|---|---|
| Ex. 9 | 35 | 6.3 | 4.5 | 95.4 | 0.1 | 0.0 | 0.0 | 0.0 | 95.5 | 99.9 |
| Ex. 10 | 0 | 75 | 10.0 | 89.3 | 0.7 | 0.0 | 0.0 | 0.0 | 90.0 | 99.2 |

As is clear from the results of Examples 9 and 10 shown in Table 7, 2BMN can be efficiently obtained with high conversion and selectivity by appropriately changing the reaction time regardless of whether the reaction temperature is relatively low or high.

Examples 11 to 13

The reaction was carried out in the same manner as in Example 1, except that the kind of solvent and the reaction time were changed as shown in Table 8. The obtained reaction solution was analyzed in the same manner as in Example 1. The results are shown in Table 8.

TABLE 8

| Ex. | solvent | reaction time [min] | HPLC analysis results of reaction solution [Area %] 2MN | 2BMN | 2DBMN | 1BMN | 1B2BMN | Others | conversion [%] | selectivity [%] |
|---|---|---|---|---|---|---|---|---|---|---|
| Ex. 11 | AcOMe | 25 | 9.9 | 85.7 | 0.8 | 0.0 | 0.0 | 3.7 | 89.8 | 99.1 |
| Ex. 12 | AcOMe | 15 | 9.1 | 87.7 | 0.6 | 0.0 | 0.0 | 2.6 | 90.7 | 99.3 |
| Ex. 13 | AcOMe | 10 | 9.4 | 87.5 | 0.6 | 0.0 | 0.0 | 2.5 | 90.3 | 99.4 |

As is clear from the results of Examples 11 to 13 shown in Table 8, 2BMN can be efficiently obtained with high conversion and selectivity, even when methyl acetate is used as a solvent.

Example 14

The reaction was carried out in the same manner as in Example 12, except that the reaction atmosphere was changed as shown in Table 9. The obtained reaction solution was analyzed by Analysis Method 2. The results are shown in Table 9.

TABLE 9

| Ex. | atmosphere | HPLC analysis results of reaction solution [Area %] 2MN | 2BMN | 2DBMN | 1BMN | 1B2BMN | Others | conversion [%] | selectivity [%] |
|---|---|---|---|---|---|---|---|---|---|
| Ex. 12 | air | 9.1 | 87.7 | 0.6 | 0.0 | 0.0 | 2.6 | 90.7 | 99.3 |
| Ex. 14 | nitrogen | 15.3 | 79.6 | 1.4 | 1.2 | 0.3 | 2.18 | 84.4 | 96.5 |

As is clear from the results of Examples 12 and 14 shown in Table 9, 2BMN can be efficiently obtained with high conversion and selectivity by carrying out the reaction in an oxygen-containing atmosphere.

Examples 15 to 21

The reaction was carried out in the same manner as in Example 12, except that the concentration of 2MN, the amount of halogenating agent used, the reaction temperature and the reaction time were changed as shown in Table 10. The obtained reaction solution was analyzed in the same manner as in Example 12. The results are shown in Table 10.

TABLE 10

| Ex. | solvent | 2MN concentration [mol/L] | halogenating agent [eq.] | reaction temperature [° C.] | reaction time [min] | HPLC analysis results of reaction solution [Area %] 2MN | 2BMN | 2DBMN | 1BMN | 1B2BMN | Others | conversion [%] | selectivity [%] |
|---|---|---|---|---|---|---|---|---|---|---|---|---|---|
| Ex. 15 | AcOMe | 0.25 | 1.00 | 10 | 10 | 50.3 | 44.6 | 0.2 | 1.6 | 0.9 | 2.5 | 48.5 | 94.5 |
| Ex. 16 | AcOMe | 0.25 | 1.00 | 25 | 10 | 8.0 | 82.5 | 2.9 | 0.2 | 1.8 | 4.5 | 91.6 | 94.3 |
| Ex. 17 | AcOMe | 0.25 | 1.00 | 40 | 10 | 8.4 | 82.3 | 3.6 | 0.1 | 1.8 | 3.7 | 91.3 | 93.7 |

TABLE 10-continued

| Ex. | solvent | 2MN concen-tration [mol/L] | halogen-ating agent [eq.] | reaction temper-ature [° C.] | reaction time [min] | HPLC analysis results of reaction solution [Area %] 2MN | 2BMN | 2DBMN | 1BMN | 1B2BMN | Others | conver-sion [%] | select-ivity [%] |
|---|---|---|---|---|---|---|---|---|---|---|---|---|---|
| Ex. 18 | AcOMe | 0.25 | 1.00 | 40 | 7 | 7.7 | 83.4 | 3.8 | 0.1 | 1.5 | 3.4 | 92.0 | 93.8 |
| Ex. 19 | AcOMe | 0.25 | 1.00 | 40 | 5 | 7.9 | 83.5 | 3.7 | 0.1 | 1.7 | 3.1 | 91.8 | 93.8 |
| Ex. 20 | AcOMe | 0.25 | 1.00 | 40 | 3 | 14.0 | 79.0 | 2.5 | 0.3 | 1.5 | 2.8 | 85.6 | 94.8 |
| Ex. 21 | AcOMe | 0.25 | 1.00 | 55 | 10 | 8.8 | 81.5 | 4.1 | 0.1 | 1.8 | 3.6 | 90.9 | 93.1 |

As is clear from the results of Examples 15 to 21 shown in Table 10, 2BMN can be efficiently obtained with high selectivity by appropriately changing the reaction temperature and the reaction time.

Example 22

A sealed glass reactor equipped with a cooling condenser, heating jacket and stirrer was charged with a mixed solvent of acetonitrile (32 mL)/water (8 mL). Then, 2BMN (8.00 g, 36.18 mmol) and sodium cyanide (2.12 g, 43.42 mmol were added thereto, the jacket temperature was raised to 60° C. under stirring, and the reaction was allowed to proceed for 4 hr at the same temperature.

The obtained reaction solution was analyzed by Analysis Method 2, and the result showed that the obtained reaction solution contained NpAN as the main product (conversion 99.1%).

NpAN:

$^1$H-NMR (400 MHz, $CDCL_3$): δ 7.87-7.83 (m, 4H), 7.54-7.50 (m, 2H), 7.39 (dd, J=6.5 Hz, 10.5 Hz, 1H), 3.92 (s, 2H)

INDUSTRIAL APPLICABILITY

According to the method for producing 2-(halogenated methyl)naphthalenes of the present invention, 2-(halogenated methyl)naphthalenes, which are useful as synthetic raw materials or synthetic intermediates for pharmaceuticals, can be produced safely, inexpensively and efficiently with high conversion and selectivity from 2-methylnaphthalene. Moreover, according to the method for producing 2-naphthylacetonitrile of the present invention, 2-naphthylacetonitrile, which is useful as a synthetic raw material or synthetic intermediate for pharmaceuticals, can be produced safely, inexpensively and efficiently with high conversion and selectivity in high yield. Since 2-(halogenated methyl) naphthalenes and 2-naphthylacetonitrile obtained in the present invention can be used as synthetic raw materials or synthetic intermediates for various pharmaceuticals, the method of the present invention is industrially useful.

EXPLANATION OF SYMBOLS

1 preparation tank
2 pump
3 flow reactor
4 light irradiation mechanism
5 recovery tank
6 preparation tank (cyanation process)
7 pump (cyanation process)
8 flow reactor (cyanation process)
9 recovery tank (cyanation process)

The invention claimed is:

1. A method for producing a 2-(halogenated methyl) naphthalene of formula (1):

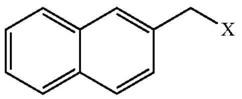

(1)

wherein
X is a halogen atom,
the method comprising:
flow synthesis reaction in an open system of 2-methylnaphthalene with a halogenating agent under light irradiation, in methyl acetate,
wherein
a temperature of the flow synthesis reaction is from −20° C. to 55° C., and
the flow synthesis reaction does not comprise an additive.

2. The method according to claim 1, wherein the halogenating agent is a brominating agent.

3. The method according to claim 1, wherein the light irradiation is performed with light having a wavelength of from 280 nm to 700 nm.

4. A method for producing 2-naphthylacetonitrile, comprising:
flow synthesis reaction in an open system of 2-methylnaphthalene with a halogenating agent under light irradiation, in methyl acetate to produce a 2-(halogenated methyl) naphthalene of formula (1):

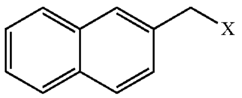

(1)

wherein X is a halogen atom; and
cyanation of the 2-(halogenated methyl) naphthalene with a cyanating agent, in a solvent, wherein
a temperature of the flow synthesis reaction is from −20° C. to 55° C., and
the flow synthesis reaction does not comprise an additive.

* * * * *